United States Patent [19]

Iga et al.

[11] Patent Number: 4,877,561
[45] Date of Patent: Oct. 31, 1989

[54] METHOD OF PRODUCING LIPOSOME

[75] Inventors: Katsumi Iga, Suita; Naoru Hamaguchi; Yasuaki Ogawa, both of Ibaraki, all of Japan

[73] Assignee: Takeda Chemical Industries, Ltd., Osaka, Japan

[21] Appl. No.: 33,498

[22] Filed: Apr. 2, 1987

[30] Foreign Application Priority Data

Apr. 2, 1986 [JP] Japan .................................. 61-76102

[51] Int. Cl.$^4$ ........................ A61K 9/66; A61K 37/22; A61K 45/05; B01J 13/02
[52] U.S. Cl. ..................................... 264/4.3; 264/4.6; 424/7.1; 424/85.2; 424/94.3; 424/450; 428/402.2; 436/829; 514/885
[58] Field of Search .................. 264/4.3, 4.6; 424/450; 436/829

[56] References Cited

U.S. PATENT DOCUMENTS

| | | | |
|---|---|---|---|
| 4,217,344 | 8/1980 | Vanlerberghe et al. | 264/4.6 X |
| 4,224,179 | 9/1980 | Schneider | 264/4.6 |
| 4,235,871 | 11/1980 | Papahadjopoulos et al. | 424/450 |
| 4,241,046 | 12/1980 | Papahadjopoulos et al. | 424/450 |
| 4,394,448 | 7/1983 | Szoka, Jr. et al. | 424/450 X |
| 4,515,736 | 5/1985 | Deamer | 264/4.3 |
| 4,565,696 | 1/1986 | Heath et al. | 424/450 X |
| 4,673,567 | 6/1987 | Jizomoto | 264/4.3 X |

FOREIGN PATENT DOCUMENTS

| | | | |
|---|---|---|---|
| 0069307 | 1/1983 | European Pat. Off. | 424/450 |
| 0092453 | 10/1983 | European Pat. Off. | |
| 0171710 | 2/1986 | European Pat. Off. | |
| 2561101 | 9/1985 | France | |
| 57-82310 | 5/1982 | Japan | |
| 57-82311 | 5/1982 | Japan | |

*Primary Examiner*—Richard D. Lovering
*Attorney, Agent, or Firm*—Wenderoth, Lind & Ponack

[57] ABSTRACT

Liposomes with an increased drug trap can be prepared by adding a readily volatile organic solvent to a drug-containing liquid with liposomes dispersed therein to cause gel formation and then removing said organic solvent by evaporation.

13 Claims, No Drawings

METHOD OF PRODUCING LIPOSOME

This invention relates to a method of producing liposomes. More particularly, the object of the invention is to provide liposomes with an increased drug trap ratio in a practically advantageous manner.

The so-far known liposome species include MLV (multilamellar vesicle), SUV (small unilamellar vesicle) and LUV (large unilamellar vesicle; also called REV: reverse-phase evaporation vesicle) and a presentation of their characteristics and the methods of their production can be found in "Cell Engineering," Vol. 2, No. 9, 1136 (1983), for instance. A further liposome species differing from the above three species and called SPLV (stable plurilamellar vesicle) has recently become known (Japanese Patent Application under PCT laid open under Kohyo No. 59-500952).

Liposomes of these kinds as obtained by the so-far known methods have drawbacks with respect to their manufacturing and their application as drug dosage forms. The MLV, when applied for drug encapsulation, gives a low drug trap ratio and, moreover, has poor stability. The SUV gives a low drug trap ratio, too. Some kinds of drugs can hardly be incorporated into the SUV. The REV is known to be a liposome species giving relatively high drug trap ratios. Its production is performed by dissolving a phospholipid in an organic solvent, adding an aqueous layer to give a w/o emulsion and further evaporating the organic solvent from said emulsion (Japanese Patent Application laid open under Kokai No. 55-118415). This process involves the step of preparing a fine w/o emulsion using an organic solvent. Therefore, the following problems, among others, may be pointed out in the REV preparation: (1) it needs an ultrasonic emulsification step, (2) it needs a large quantrty of an organic solvent and (3) it needs fine adjustment of the vacuum during the solvent evaporation process. Any of, these drawbacks makes it difficult to produce the REV on a large scale at a time. The SPLV process encounters a similar problem that it needs a larger quantity of organic solvent as compared with lipids and also a problem of necessity of using restricted kinds of lipids which have low phase transition temperatures, such as egg yolk lecithin.

Thus, the liposomes, when produced by the so-far known methods, still have problems as mentioned above, i.e. the problems of their manufacturing and of their application as microcapsules for drugs. Therefore, the present inventors conducted intensive investigations and, as a result, they found a method of producing stable liposomes with an increased drug trap ratio and good reproducibility, irrespective of smallness or largeness of the production scale, which comprises adding a small amount of a readily volatile organic solvent to an MLV produced by a known method or to SUV obtained by ultrasonic treatment and then removing the organic solvent from the resulting gel by evaporation under ordinary reduced pressure or in a nitrogen gas stream. Further studies have now resulted in completion of the present invention.

The present invention thus consists in a method of producing liposomes with increased drug trap ratio, which comprises adding a readily volatile organic solvent to a drug-containing liquid phase with liposomes dispersed therein, and thereafter removing said organic solvent by evaporation.

The "drug-containing liquid phase with liposomes dispersed therein" means a drug-containing liquid in which the liposomes with or without drug incorporation therein to be used in the production process are dispersed. Said liposomes may be those produced by any of the known methods and, in particular, MLV or SUV liposomes are used advantageously. For instance, the MLV to be used in practicing the invention can be obtained by a known method; 5–100 parts by volume of an aqueous drug solution is added to 1 part by weight of a lipid in the thin film form which is previously obtained by the film method, and then MLV is obtained by stirring the mixture of the lipid and the drug solution with a vortex mixer. In this instance, the drug concentration can suitably be selected depending on the kind thereof. The SUV can be obtained by comminuting the above MLV, for example by treatment on a probe-type ultrasonic generator (20 KHz). The thus obtained MLV or SUV can be used as a starting material for the production of the liposomes in the present invention. Any other vesicles capable of forming lipid bilayers can also be used as starting materials for the production of the liposomes in the present invention in the same manner as the abovementioned MLV and SUV, even when said vesicles are low in drug trap ratio or unstable. As such starting materials, there may be mentioned, for example, liposomes obtained by the ether addition method [Biochimica et Biophysica Acta, Vol. 443, page 629 (1976)], liposomes obtained by dispersing a lyophilizate in water (Japanese Patent Application laid open under Kokai No. 53-142514) and liposomes obtained by the freezing-thawing method (Japanese Patent Application laid open under Kokai No. 51-86117).

In addition, drug-free liposomes, which are prepared from the lipid and the drug-free solution, can also be used as a starting material. Such drug-free liposomes may be dispersed in a drug-containing liquid. In the present invention, a pH control agent, an, antioxidant, a substance for adjustment of osmotic pressure or an antiseptic, etc. may be added to the drug-containing liquid, if necessary.

Regarding the drug to be used in the practice of the invention, there is no particular limitation; it may be a hydrophilic drug or a lipophilic one. However, the method of the invention is most preferably applicable to hydrophilic drugs having an "octyl alcohol/water-distribution ratio" lower than 10 as the logarithmic value. Examples of such hydrophilic drug include various antiinflammatory analgesics, lymphokines, anticancer agents, immunopotentiators, physiologically active peptides, antibiotics, antiprotozoa agents, enzymes, antiallergic drugs and so on. More detailed examples of the hydrophilic drug are lymphokines such as interferons and interleukin 2, antiinflammatory analgesic peptides such as manganese-containing superoxide dismutase (SOD), superoxide dismutase-PEG (SOD-PEG) which is a derivative of SOD (Japanese Patent Application laid-open No. 58-16685 and European Patent Publication No. 0070656), lipomodulins; anticancer agents such as cisplatin, mitomycin C, 5-FU, adriamycin, actinomycin and bleomycin; immunopotentiators such as muramyldipeptides and muramyltripeptides; physiologically active peptides such as thyroid hormone-releasing hormone (TRH), leuprolide, insulin and DN-1417 (Japanese Patent Application laid-open No. 57-132658 and European Patent Publication No. 0094157); β-lactam antibiotics such as sulbenicillin, cefotiam, cefmenoxime and sulfazecin; aminoglycoside antibiotics such as gentamicin, streptomycin and kanamycin; vitamins (e.g. cyanocobalamin), antiprotozoal agents (e.g. meglumine antimonate); enzymes (e.g. alkaline phosphatase); anticoagulants (e.g. heparin); antiallergics; and other general-use drugs (e.g. glutathione).

The lipid material to be used in the practice of the invention may be any one that can form lipid bilayers. For example, there may be mentioned phospholipids derived from egg yolk, soybean or other animal or vegetable tissues, such as phosphatidylcholines, phosphatidylethanolamines, phosphatidylinositols, phosphatidylserines and sphingomyelins; mixtures of these, such as egg yolk lecithin; hydrogenated lecithins; dipalmitoylphosphatidylcholines, semisynthetic distearoylphosphatidylcholines; and other lipids than the above-mentioned phospholipids, such as cholesterol, monoglycerides, diglycerides and triglycerides. These may be used either singly or in admixture.

In accordance with the invention, a gel is then formed by adding a readily volatile organic solvent to a "drug-containing liquid phase with liposomes dispersed therein" such as mentioned above.

The readily volatile organic solvent to be used here may be any one that has high affinity for lipids and can evaporate more readily than water. The miscibility with water does not matter. Generally, organic solvents having a boiling point not higher than 100° C. are used advantageously. For example, there may be mentioned ethers (e.g. diethyl ether, isopropyl ether), chloroform, acetone and alcohols (e.g. methyl alcohol, ethyl alcohol). These solvents may be used alone or as a mixture. Among them, diethyl ether and acetone are particularly preferred.

The readily volatile organic solvent is added generally in an amount of about 1–30 parts by volume per 10 parts by volume of the drug-containing liquid with liposomes dispersed therein, preferably in an amount of 2–10 parts by volume on the same basis. The mixture is then stirred and/or shaken with a vortex mixer or some other appropriate apparatus generally for tens of seconds to several minutes to give a homogeneous gel. As a result of this treatment, the vesicle structure of the liposomes used as a raw material is relaxed or disintegrated by the organic solvent, whereby a uniform gel state is produced.

The readily volatile organic solvent is then removed by evaporation. As the method of evaporation, there may be mentioned the vacuum evaporation method using a rotary evaporator, which is in common use, or a vibrating vacuum evaporator and the evaporation method comprising blowing a nitrogen gas stream. In particular, in blowing a nitrogen gas stream, application of vibrations from the outside using a vortex mixer or a bath-type sonicator can result in more efficient removal of the organic solvent. The gel formation and organic solvent removal by evaporation are preferably carried out at a temperature not lower than the phase transition point of the lipid used. Thus, for instance, temperatures not lower than room temperature are preferable for egg yolk lecithin and soybean lecithin, temperatures not lower than 50° C. for dipalmitoylphosphatidylcholines, and temperatures not lower than 60° C. for distearoylphosphatidyl-cholines.

The removal of the organic solvent leads to reconstitution of liposomes and, on that occasion, increased drug trap ratios are achieved as compared with the case of MLV or SUV used as the starting material. Thus, the liposomes with increased drug trap ratios are obtained according to the invention.

The thus-obtained liposomes with a drug included therein may, if necessary, be comminuted by using an ultrasonic homogenizer or some other homogenizer or be adjusted to a favorable grain size by filtration through a filter. Although the liposomes can be used as they are, they may be made up into such dosage forms as injections, oral preparations and suppositories after removing that portion of the drug which remains unincluded in the liposomes, by centrifugation, gel filtration or dialysis, for instance.

The liposomes obtained by the production method according to the invention show higher drug trap ratios as compared with those obtained by the conventional MLV, SUV or REV method and are advantageous from the practical viewpoint in utilizing them as microcapsules. In the present invention, drug trap ratios are calculated by the following equation:

Trap ratio (%) =

$$\frac{\text{(Total amount of drug in liposome dispersion)} - \text{(Amount of free drug in liposome dispersion)}}{\text{(Total amount of drug used in liposome production)}} \times 100$$

Furthermore, the method according to the invention has the following features as compared with the conventional production methods:

(a) The preparation of a w/o emulsion as required in the REV process is not always necessary.
(b) The fine adjustment of the degree of vacuum in distilling off the organic solvent as required in the REV process is unnecessary.
(c) While the REV process is limited in liposome production size per batch, the method according to the invention can be easily conducted on an increased scale.
(d) Unlike the case of REV or SPLV, the use of an organic solvent in large amounts is not necessary.
(e) Many kinds of organic solvents can be used. Even when the drug is one that can be readily inactivated by an organic solvent, the use of a hydrophilic organic solvent such as acetone or ethyl alcohol can prevent such inactivation. For these and other reasons, it is possible to select an appropriate organic solvent while taking the characteristics of the drug to be included into consideration.
(f) Generally, when a lipid relatively low in solubility in an organic solvent, for example a lipid having a high phase transition point (in particular, a lipid of the saturated type, such as DPPC or DSPC), is used, the organic solvent is needed in large amounts for the dissolution of the lipid as in the REV process. In accordance with the present method, however, any lipid can be used and it is possible to use a small amount of the organic solvent.

EXAMPLES

The following working examples and test examples will illustrate the invention in further detail.

EXAMPLE 1

A thin lipid film was formed on the glass wall of a 50-ml eggplant-shaped flask using 10 ml of a chloroform solution containing 1% of a 9:1 (w/w) mixture of dipalmitoylphosphatidylcholine and distearoylphosphatidylcholine. To the flask was added 3 ml of a 50 mM solution of 6-carboxyfluorescein (6-CF) as adjusted to pH 7. The flask contents were stirred and shaken well in a bath-type sonicator maintained at 55° C. to cause inclusion of 6-CF. Thus were produced MLV liposomes dispersed in the 6-CF solution. To the thus obtained MLV dispersion was added 3 ml of ethyl ether at the same temperature as above. Stirring and shaking of the mixture with a vortex mixer for about 1 minute gave a homogeneous gel. The ethyl ether in the gel was removed by evaporation caused by blowing $N_2$ gas against the gel with vibration by means of the sonicator. About 3 ml of a dispersion of liposomes with 6-CF included therein was obtained. This was diluted with 2 ml of physiological saline and the dilution was filtered through a 1.2-micron filter (Acrodisc ®; Gelman) and then dialyzed against 1,000 ml of physiological saline using a dialyzing membrane (Spectrapor ®; Spectrum Medical) for 24 hours to give liposomes with a 6-CF trap ratio of 28.9%.

EXAMPLE 2

The procedure of Example 1 was followed using a chloroform solution containing 1% of a 7:3 (w/w) mixture of dipalmitoylphosphatidylcholine and distearoylphosphatidylcholine and a processing temperature of 60° C. to give liposomes with a 6-CF trap ratio of 32.2%.

EXAMPLE 3

The procedure of Example 1 was followed using a chloroform solution containing 1% of distearoylphosphatidylcholine and a processing temperature of 70° C. to give liposomes with a 6-CF trap ratio of 37.7%.

EXAMPLE 4

The procedure of Example 1 was followed using 1 ml of a chloroform solution containing 10% of egg yolk lecithin in lieu of the semisynthetic lecithin used in Example 1 with further modifications such that ethyl ether was used in an amount of 1 ml and that room temperature was used as the processing temperature. Thus were obtained liposomes with a 6-CF trap ratio of 30.1%.

EXAMPLE 5

Several batches of MLV were produced by the method of Example 4. To a 30-ml portion of MLV as obtained by combining such batches was added 10 ml of ethyl ether and the mixture was processed in the same manner as in Example 4 to give liposomes with an improved 6-CF trap ratio.

EXAMPLE 6

Liposomes were obtained with an improved 6-CF trap ratio in the same manner as in Example 4 except that 3 ml of acetone was used in lieu of the ethyl ether used in Example 4.

EXAMPLE 7

An SUV obtained by comminuting the MLV produced in Example 4 by means of a probe-type ultrasonic shaker was used and processed in the same manner as in Example 4 to give liposomes with an improved 6-CF trap ratio.

EXAMPLE 8

A thin lipid film was formed on the glass wall of a 50-ml eggplant-shaped flask using 1.5 ml of a chloroform solution containing 1% of a 9:1 (w/w) mixture of dipalmitoylphosphatidylcholine and distearoylphosphatidylcholine. To the flask was added 0.5 ml of an aqueous solution of interleukin 2 (content: 308 µg protein/ml; kind of solution: 5 mM ammonium acetate solution containing human serum albumin, pH 5.0). The flask contents were stirred and shaken well in a bath-type sonicator maintained at 55° C to thereby cause inclusion of interleukin 2. Thus was obtained an MLV dispersion in the above drug solution. Then, 0.5 ml of ethyl ether was added to this MLV dispersion at the same temperature and the resultant mixture was stirred and shaken with a vortex mixer for about 1 minute to give a homogeneous gel. The ethyl ether in the gel was removed by evaporation caused by blowing $N_2$ gas against the gel with further vibration by means of the sonicator. There was obtained about 3 ml of a dispersion of liposomes with interleukin 2 included therein. After further addition to this 10 ml of the interleukin-free solution used for preparing the above aqueous interleukin 2 solution (dispersant for interleukin 2 liposomes) for dilution, the whole mixture was centrifuged on an ultracentrifuge (Sorvall ®; Sorvall) at 30,000 r.p.m. for 30 minutes to give liposomes with an improved interleukin 2 trap ratio.

EXAMPLE 9

A thin lipid film was formed on the glass wall of a 50-ml eggplant-shaped flask using 10 ml of a chloroform solution containing 1% of a 9:1 (w/w) mixture of dipalmitoylphosphatidylcholine and distearoylphosphatidylcholine. To the flask was added 3 ml of an aqueous solution of manganese-SOD (content: 6 mg protein/ml; kind of solution: 67 mM phosphate buffer, pH 7.0), and the flask contents were stirred and shaken well in a bath-type sonicator maintained at 55° C. to give a dispersion of MLV liposomes in said drug solution with manganese-SOD included therein. To the thus-obtained MLV dispersion, there was added 3 ml of ethyl ether, and the resultant mixture was stirred with shaking by a vortex mixer for about 1 minute to give a homogeneous gel. The ethyl ether in the gel was removed by evaporation caused by blowing $N_2$ gas against the gel with further vibration by means of the sonicator to give about 3 ml of a dispersion of liposomes with manganese-SOD included therein. To this was further added 10 ml of physiological saline, followed by centrifugation on an ultracentrifuge (Sorvall ®; Sorvall) at 30,000 r.p.m. for 30 minutes. There were obtained liposomes with a manganese-SOD trap ratio of 25.3%.

EXAMPLE 10

A thin lipid film was formed on the glass wall of a 50-ml eggplant-shaped flask using 10 ml of a chloroform solution containing 1% of a 9:1 (w/w) mixture of dipalmitoylphsophatidylcholine and distearoylphosphatidylcholine. To the flask was then added 3 ml of an aqueous solution of manganese-SOD-PEG(5000) (content: 0.5 mg protein/ml; kind of solution: 67 mM phosphate buffer, pH 7.2). The flask contents were stirred and shaken well in a bath-type sonicator maintained at 55° C. to give a dispersion of MLV liposomes with manganese-SOD-PEG(5000) included therein. To the thus-obtained MLV dispersion, there was added 3 ml of ethyl ether at the same temperature and the mixture was stirred with shaking by a vortex mixer for about 1 minute to give a homogeneous gel. The ethyl ether in the gel was removed by evaporation caused by blowing $N_2$ gas against the gel with vibration by means of the sonicator, to give about 3 ml of a dispersion of liposomes with manganese-SOD-PEG(5000) included therein. To this was further added 10 ml of physiological saline and the resultant mixture was subjected to centrifugation in the same manner as in Example 8 to give liposomes with a manganese-SOD-PEG(5000) trap ratio of 27.0%.

EXAMPLE 11

A thin lipid film was formed on the glass wall of a 50-ml eggplant-shaped flask using 10 ml of a chloroform solution containing 1% of a 9:1 (w/w) mixture of dipalmitoylphosphatidylcholine and distearoylphosphatidylcholine. To the flask was added 3 ml of an aqueous solution of cisplatin (content: 0.5 mg/ml; kind of solution: physiological saline). The flask contents were stirred and shaken well in a bath-type sonicator maintained at 55° C. to give a dispersion of MLV liposomes in said drug solution with the aqueous cisplatin solution included therein. Ethyl ether (3 ml) was added to the thus-obtained MLV dispersion at the same temperature and the mixture was stirred with shaking by a vortex mixer for about 1 minute to give a homogeneous gel. The ethyl ether in the gel was then removed by evaporation caused by blowing $N_2$ gas against the gel with vibration by means of the sonicator to give about 3 ml of a dispersion of liposomes with cisplatin included therein. To this was added 2 ml of physiological saline and the mixture was filtered through a 1.2-micron filter (Acrodisc®; Gelman) and further dialyzed against 1,000 ml of physiological saline for 24 hours using a dialyzing membrane (Spectrapor®; Spectrum Medical). Thus were obtained liposomes with a cisplatin trap ratio of 29.8%.

EXAMPLE 12

The procedure of Example 11 was followed using a chloroform solution containing 1% of a 7:3 (w/w) mixture of dipalmitoylphosphatidylcholine and distearoylphosphatidylcholine and a processing temperature of 60° C. to give liposomes with a cisplatin trap ratio of 32.4%.

EXAMPLE 13

The procedure of Example 11 was followed using a chloroform solution containing 1% of distearoylphosphatidylcholine and a processing temperature of 70° C. to give liposomes with a cisplatin trap ratio of 35.2%.

EXAMPLE 14

MLV-type liposomes with no drug included therein were produced by adding 2 ml of physiological saline to the thin lipid film prepared in the same manner as in Example 1, followed by processing in the same manner as in Example 1. Thereto was added 1 ml of 50 mM 6-CF solution (pH 7), and an MLV dispersion in the 6-CF solution was prepared without inclusion of 6-CF. Using the thus-obtained MLV dispersion and following the procedure of Example 1, there was obtained liposomes with a 6-CF trap ratio of 21.3%.

EXAMPLE 15

A thin lipid film was formed on the glass wall of a 50-ml eggplant-shaped flask using 10 ml of a chloroform solution containing 1% of a 9:1 (w/w) mixture of dipalmitoylphosphatidylcholine and distearoylphosphatidylcholine. To the flask was added 3 ml of a 50 mM solution of 6-carboxyfluorescein (6-CF) as adjusted to pH 7. The flask contents were stirred and shaken well in a bath-type sonicator maintained at 55° C. to cause inclusion of 6-CF. Thus were produced MLV liposomes dispersed in the 6-CF solution. To the thus obtained MLV dispersion was added 1 ml of ethyl alcohol at the same temperature as above. Stirring and shaking of the mixture with a vortex mixer for about 1 minute gave a homogeneous gel. The ethyl alcohol in the gel was removed by evaporation caused by blowing $N_2$ gas against the gel with vibration by means of the sonicator, ten 0.2 ml portions of water being added to the gel. About 3 ml of a dispersion of liposomes with 6-CF included therein was obtained. This was diluted with 2 ml of physiological saline and the dilution was filtered through a 1.2-micron filter (Acrodisc®; Gelman) and then dialyzed against 1,000 ml of physiological saline using a dialyzing membrane (Spectrapor®; Spectrum Medical) for 24 hours to give liposomes with a 6-CF trap ratio of 13.5%.

TEST EXAMPLE 1

To 3 ml of the MLV dispersion prepared by the method described in Example 4, there was added ethyl ether in an amount within the range of 0.1 ml to 1.0 ml to thereby investigate the dependency of the ability thereof to cause gel formation and the ability to form liposomes upon removal of the ethyl ether on the amount of the ethyl ether used. As a result, it was found that the minimum amount of ethyl ether as required for gel formation and production of liposomes in accordance with the invention is 0.3 ml, as shown in Table 1.

TABLE 1
Amount of ethyl ether used and ability to cause gel formation and liposome formation

| Amount of ethyl ether (ml) | 0.1 | 0.2 | 0.3 | 0.4 | 0.5 | 1.0 |
|---|---|---|---|---|---|---|
| Gel formation | − | − | ± | + | + | + |
| Formation of liposomes according to the invention | − | − | + | + | + | + |

− ... No gel formation
± ... Partial gel formation
+ ... Good gel formation

TEST EXAMPLE 2

The liposomes according to the invention with 6-CF included therein as produced in Examples 1, 2, 3 and 4 were assayed for 6-CF content by measuring the intensity of the fluorescence of 6-CF (1) and the 6-CF trap ratios calculated on the basis of the fluorescence measurement results (2) were compared with the trap ratios for the MLVs produced in the respective examples and for the liposomes with 6-CF included therein as prepared separately by the REV method (3) so as to have the same lipid structure. As a result, the liposomes according to the invention all showed higher trap ratios, as shown in Table 2.

(1) Determination of 6-CF content in liposomes:

Liposomes (0.1 ml) were diluted 100-fold with phosphate-buffered physiological saline (PBS), a 0.1-ml portion of the dilution was further diluted 100-fold with PBS containing 0.02% of Triton X-100, and the dilution was heated at 60° C. for 30 minutes to thereby cause disruption of liposomes. The resultant solution was measured for fluorescence intensity (Hitachi model F3000 fluorescence spectrometer; excitation wavelength 494 nm; measurement wavelength 515 nm) and the total 6-CF content in the liposome dispersion (inclusive of free 6-CF occurring unincorporated into liposomes) was determined. Separately, 0.1 ml of the liposome dispersion was diluted 10,000-fold with PBS, a 2.5-ml portion of the dilution was filtered through an ultracentrifugal filter (Centrisart ® SM13249E; Sartorius) and the filtrate was measured for fluorescence intensity; the content of free 6-CF occurring in the liposome dispersion in the unincluded state was thus determined.

(2) Method of producing REV:

A 100-mg portion of the lipid used in each of Examples 1, 2, 3 and 4 was placed in a 100-ml eggplant-shaped flask and dissolved by adding 10 ml of chloroform and 10 ml of isopropyl ether, followed by further addition of 3 ml of the 6-CF solution used in each example. The result mixture was emulsified in a probe-type ultrasonic shaker (20 KHz). Then, the organic solvents were removed by evaporation using a rotary evaporation (temperature condition: same as used in each example) and the residual dispersion was dialyzed in the same manner as in each example to give an REV with 6-CF included therein.

(3) Calculation of trap ratios:

Trap ratio (%) =

$$\frac{\text{(Total amount of 6-}CF\text{ in liposome dispersion)} - \text{(Amount of free 6-}CF\text{ in liposome dispersion)}}{\text{(Amount of 6-}CF\text{ used in liposome production)}} \times 100$$

TABLE 2

Comparison of trap ratios of 6-CF in liposomes
(in %)

| Lipid construction | Liposomes according to the invention | MLV | REV |
|---|---|---|---|
| DPPC[e]/DSPC[f] = 9/1 | 28.9[a] | 12.5[a] | 17.6 |
| DPPC/DSPC = 7/3 | 32.2[b] | — | 24.2 |
| DSPC | 37.7[c] | — | 27.2 |
| Egg yolk lecithin | 30.1[d] | — | 23.0 |

[a]Product of Example 1
[b]Product of Example 2
[c]Product of Example 3
[d]Product of Example 4
[e]Dipalmitoylphosphatidylcholine
[f]Distearoylphosphatidylcholine

TEST EXAMPLE 3

In this test example, the liposomes according to the invention with cisplatin included therein as produced in Examples 11, 12 and 13 were used. Each liposome dispersion was assayed for cisplatin by HPLC (column: Zorbax CN®; eluent: n-hexane/isopropyl alcohol=8/2; UV=254 nm) for the adduct formed by reaction of cisplatin with diethyldithiocarbamate (DDTC) (1). The cisplatin trap ratios calculated on the basis of the results of such assay were compared with those for the MLVs produced in the respective examples and for the liposomes with cisplatin included therein as prepared separately by the REV method so as to attain the same lipid structure. Thus, the data shown in Table 3 were obtained and the liposomes according to the invention always showed higher trap ratios.

(1) Determination of cisplatin content in liposomes:

Liposomes (0.1 ml) were dispersed in 5 ml of physiological saline. A 2.5-ml portion of the dispersion was subjected to freezing-thawing treatment and the liposome disruption product was filtered through a Centrisart ® filter. To 0.1 ml of the filtrate, there was added 2 ml of 0.1 N NaOH solution. After allowing the mixture to stand at room temperature for 30 minutes, the adduct formed was extracted with 5 ml of n-hexane. The extract was assayed for cisplatin by HPLC under the conditions mentioned above. Then, the total cisplatin content in the liposome dispersion was calculated. Separately, about 2.5 ml of the remaining liposome dispersion in physiological saline was filtered through a Centrisart ® filter and adduct formation under the same conditions as mentioned above. Thus was determined the content of free cisplatin remaining unincluded in liposomes in said liposome dispersion.

TABLE 3

Comparison of trap ratios of cisplatin in liposomes
(in %)

| Lipid construction | Liposomes according to the invention | MLV | REV |
|---|---|---|---|
| DDPC/DSPC = 9:1 | 29.8[a] | 8.2[a] | 17.9 |
| DPPC/DSPC = 7:3 | 32.4[b] | — | 24.6 |
| DSPC | 35.2[c] | — | 26.6 |

[a]Product of Example 11
[b]Product of Example 12
[c]Product of Example 13

What we claim is:

1. A method of producing liposomes with increased drug trap ratio, which comprises (1) providing a dispersion containing a drug and liposomes prepared from a phospholipid, (2) adding an organic solvent having a boiling point not higher than 100° C. to the dispersion to cause gel formation, and then (3) removing said organic solvent by evaporation to reconstitute liposomes.

2. The method according to claim 1, wherein the dispersion contains multilamellar vesicles (MLV).

3. The method according to claim 1, wherein the dispersion contains small unilamellar vesicles (SUV).

4. The method according to claim 1, wherein the drug is a hydrophilic drug having an octyl alcohol/water-distribution ratio lower than 10 as the logarithmic value.

5. The method according to claim 1, wherein the drug is selected from the group consisting of antiinflammatory analgesics, lymphokines, anticancer agents, immunopotentiators, phsyiologically active peptides, antibiotics, antiprotozoa agents, enzymes and antiallergics.

6. The method according to claim 5, wherein the lymphokine is interleukin 2.

7. The method according to claim 5, wherein the anticancer agent is cisplatin.

8. The method according to claim 5, wherein the antiinflammatory analgesic is manganese superoxide dismutase or superoxide dismutase-PEG.

9. The method according to claim 1, wherein the organic solvent is ethyl ether.

10. The method according to claim 1, wherein the organic solvent is acetone.

11. The method according to claim 1, wherein the organic solvent is ethyl alcohol.

12. The method according to claim 1, wherein the organic solvent is added in amount of about 1 to 30 parts by volume per 10 parts by volume of the dispersion containing a drug and liposomeses.

13. The method according to claim 12, wherein the amount of the organic solvent is 2 to 10 parts by volume on the same basis as described in claim 12.

* * * * *